United States Patent [19]

Warriner

[11] Plant 4,812

[45] Jan. 26, 1982

[54] ROSE PLANT 70-10341-18

[75] Inventor: William A. Warriner, Tustin, Calif.

[73] Assignee: Jackson & Perkins Company, Medford, Oreg.

[21] Appl. No.: 189,788

[22] Filed: Sep. 22, 1980

[51] Int. Cl.[3] ..... A01H 5/00

[52] U.S. Cl. ..... Plt./11

[58] Field of Search ..... Plt./11, 18

*Primary Examiner*—James R. Feyrer

*Attorney, Agent, or Firm*—Klarquist, Sparkman, Campbell, Leigh, Whinston & Dellett

[57] ABSTRACT

A hybrid tea rose variety having near red to shell pink blooms on medium, strong stems, blooms having extemely stiff petals and very little fragrance.

1 Drawing Figure

This present invention relates to a new and distinct variety of rose plant of the hybrid tea class which was originated by me by crossing two unnamed varieties.

The primary objective of this breeding was to produce a new rose variety of the hybrid tea class, producing numerous blooms of a distinctive pink color and strong, substantive petals. This objective was substantially achieved along with other desirable improvements as evidenced by the following unique combination of characteristics which are outstanding in the new variety and which distinguish it from its parents as well as from all other varieties of which I am aware:

1. A vigorous, upright plant of the hybrid tea class.
2. Reddish purple new foliage and large dark green mature foliage.
3. Buds and open flowers of color commonly called shell pink, equal to Royal Horticultural Society's Red Group 38C.
4. Extremely stiff petals.
5. Little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:
- *Seed parent.*—Unnamed variety.
- *Pollen parent.*—Unnamed variety.

Classification:
- *Botanical.*—Rosa hybrid.
- *Commercial.*—Hybrid tea.

FLOWER

Observations made from specimens grown at Irvine, Calif. in August, 1980.

Blooming habit: Continuous.

Bud:

- *Size.*—1" to 1⅛" when petals start to unfurl.
- *Form.*—Broad, with blunt end.
- *Color.*—When sepals first divide, Near Red 49B, except area of petals not covered by sepals, Red 46B. When half blown, upper side of petals Near Red 38C with some spots due to weather damage much darker, near Red 46B; lower side of petals near 38C to 38D.
- *Sepals.*—Color: outer surface mostly brown except where sepals overlap, Green 138B, also with stipitate glands on surface. Three appendaged sepals lightly appendaged. Two unappendaged sepals hairy edged.
- *Receptacle.*—Color: mottled brown with small area green 138B. Shape: funnel. Size: large, broad. Surface: smooth.
- *Peduncle.*—Length: medium. Surface: slightly prickly. Color: bronzy. Strength: stiff, erect, heavy.
- *Opening.*—Very stiff petals open to high centered form, rarely do outer petals extend straight out from center.

Bloom:
- *Size.*—Medium. Average open size is 4 inches.
- *Borne.*—Singly or several together.
- *Stems.*—Medium, strong.
- *Form.*—When first open, high centered. Permanence: retains its form to the end.
- *Petalage.*—Number of petals under normal conditions, 40.
- *Color.*—Center of flower: upper side of petals Red 38B; reverse side of petals 38C; base of petals yellow. General tonality from a distance 38B.
- *Variegations.*—Weather mottling or spotting.
- *Discoloration.*—General tonality at third day: outer exposed edges becoming darker to 38A.
- *Fragrance.*—Slight.

Petals:
- *Texture.*—Thick, very stiff.
- *Shape.*—Round.
- *Form.*—Tips slightly recurved.
- *Arrangement.*—Imbricated. Petaloids in center, few.
- *Persistence.*—Drop off cleanly.
- *Lastingness.*—On the plant, very long. As cut flower, very long.

Reproductive parts:
- *Anthers.*—Large. Color: yellow. Arrangement: regular around styles.

*Filaments.*—Color: yellow.
*Pollen.*—Lemon yellow.
*Styles.*—Color: very pale green.
*Stigmas.*—Color: white.

PLANT

Form: Bush.
Growth: Vigorous, upright.
Foliage: Number of leaflets on normal mid-stem leaves, 5.
*Size.*—Large.
*Quantity.*—Normal.
*Color.*—New foliage: Near Red-Purple 59A. Old foliage: Near Green 131A.
Leaflets:
*Shape.*—Oval.
*Texture.*—Upper side: leathery, flat.
*Edge.*—Serrated.
*Serration.*—Single, small.
*Petiole.*—Rachis: color: green. Underside: prickles.
*Stipules.*—Long, bearded.

*Disease resistance.*—Resistant to mildew under normal growing conditions at Irvine, Calif.
Wood:
*New wood.*—Color: light green. Bark: smooth.
*Old wood.*—Color: green. Bark: smooth.
Prickles:
*Quantity.*—On main stalks from base, ordinary. On laterals from stalk, ordinary.
*Form.*—Long base.
*Color when young.*—Brown.
*Position.*—Irregular.
Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of a vigorous upright plant, reddish new foliage, shell pink flowers with very stiff petals, and little fragrance.

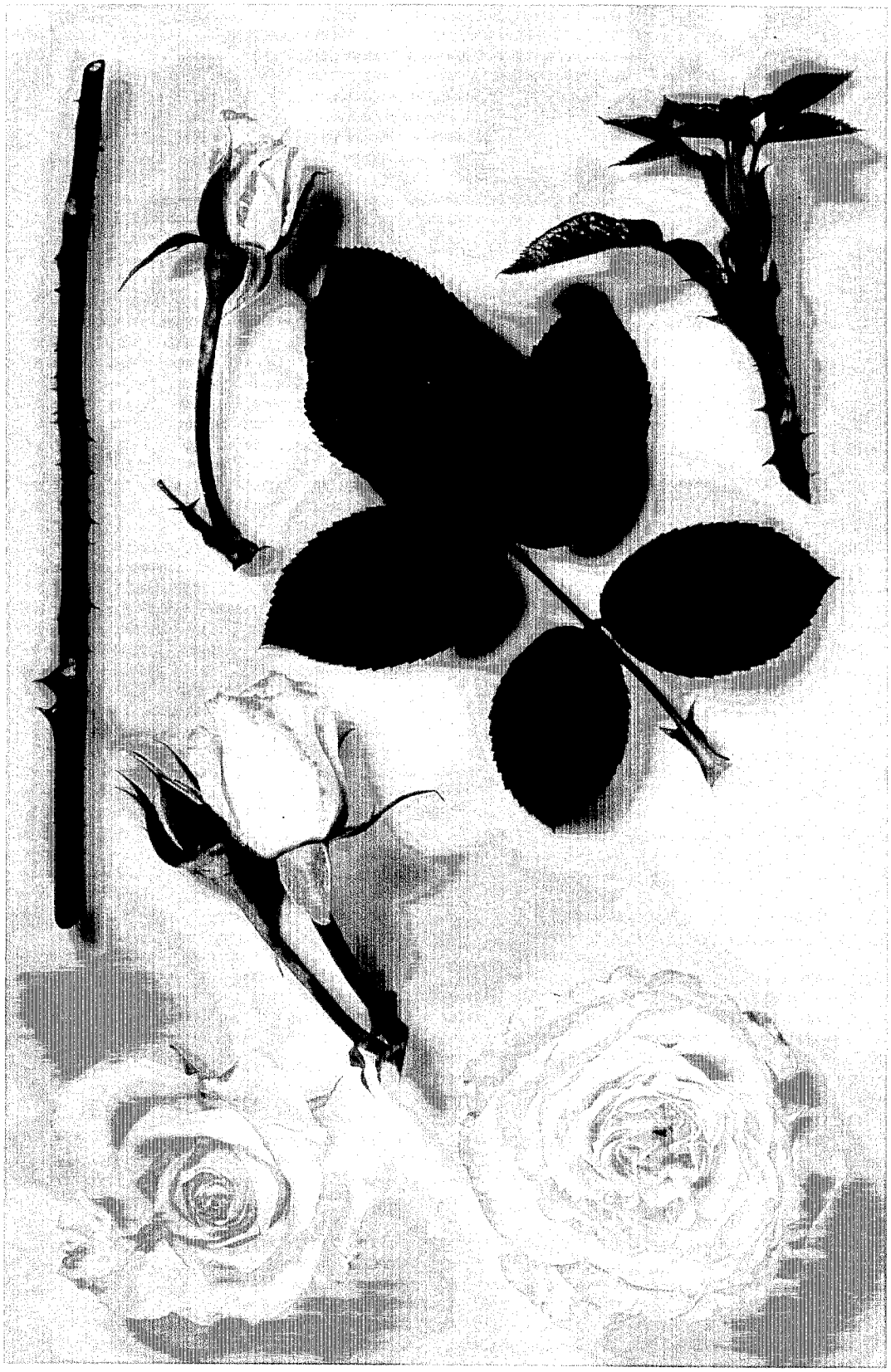

* * * * *